United States Patent
Jegelka et al.

(10) Patent No.: US 6,613,934 B1
(45) Date of Patent: Sep. 2, 2003

(54) ENANTIOMERICALLY ENRICHED MALONIC ACID MONOESTERS SUBSTITUTED BY A TERTIARY HYDROCARBON RADICAL, AND THEIR PREPARATION

(75) Inventors: Udo Jegelka, Recklinghausen (DE); Wolfgang Kleemiss, Haltern (DE); Bruno Klotz-Berendes, Werne (DE); Marcel Feld, Cologne (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 08/872,057

(22) Filed: Jun. 10, 1997

(30) Foreign Application Priority Data

Jun. 10, 1996 (DE) .......................... 196 23 142

(51) Int. Cl.$^7$ .............................................. C07C 69/76
(52) U.S. Cl. ......................... 560/82; 560/190; 435/135
(58) Field of Search .................... 560/190, 82; 435/135

(56) References Cited

U.S. PATENT DOCUMENTS 5,607,943 A  * 3/1997 Losel et al. ................. 514/301

FOREIGN PATENT DOCUMENTS

| EP | 0 050 799 A | 5/1982 |
| SE | 453 599 B | 2/1988 |

OTHER PUBLICATIONS

Kitazume, Tomoya et al: "Microbial Approach to the Practical Monofluorinated Chiral Synthons", J. Org Chem. (1986), 51(7), pp. 1003–1006, XP002114665.

Regis Leung–Toung et al.: "Flash vacuum pyrolysis of tert–butyl beta–ketoesters: Sterically protected alpha oxoketenes", Tetrahedron., Bd. 48, Nr. 36, 1992, Seiten 7641–7654, XP002114666, Oxford GB.

Database WPI Section Ch, Week 8224, Derwent Publications Ltd., London, GB: Class B05, AN 82–004555 XP002114667 & HU 22 369 A (Richter Gedeon Vegyeszeti Gyar), 28. Mai 1982.

Klotz–Berendes, Bruno et al: "Enzymic synthesis of Optically active monoalkylated malonic monoesters" Tetrahedron: Asymmetry (1997), 8(11), 1821–1823, XP002114677.

* cited by examiner

*Primary Examiner*—Samuel Barts
(74) *Attorney, Agent, or Firm*—Oblon, Spivak, McClelland, Maier & Neustadt, P.C.

(57) ABSTRACT

The invention relates to enantiomerically enriched malonic acid monoesters α-monosubstituted by a tertiary hydrocarbon radical, or their salts, of the general formula I:

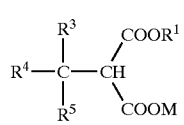

in which $R^1$, $R^3$, $R^4$ and $R^5$ are identical or different hydrocarbon radicals, and wherein any two of the radicals $R^3$, $R^4$ and $R^5$ may alternatively be present as a carbocyclic ring together with the quaternary carbon atom which they substitute, and M is hydrogen, one equivalent of a metal or an optionally substituted ammonium ion. The invention further relates to a process for the preparation of the enantiomerically enriched α-monosubstituted malonic acid monoesters, or their salts, by enzymatic partial hydrolysis of the corresponding diesters.

23 Claims, No Drawings

ENANTIOMERICALLY ENRICHED MALONIC ACID MONOESTERS SUBSTITUTED BY A TERTIARY HYDROCARBON RADICAL, AND THEIR PREPARATION

BACKGROUND OF THE INVENTION

1. Field of the Invention

The invention relates to enantiomerically enriched malonic acid monoesters substituted by a tertiary hydrocarbon radical, and their salts, and to a process for their preparation from the corresponding prochiral malonic acid diesters by enzymatic partial hydrolysis (or partial saponification).

2. Description of the Background

Enantiomerically enriched compounds are of considerable importance as synthetic units in the pharmaceutical and agrochemical sectors, and as chiral auxiliaries. Possible starting materials for enantiomerically enriched α-monosubstituted or α,α-disubstituted malonic acid monoesters are the corresponding diesters, which contain a prochiral carbon atom with two identical carboxylic acid ester groups and two other substituents which differ from one another and from the carboxylic acid ester groups. Partial saponification to the monoester produces a center of chirality and enantioselective partial hydrolysis gives enantiomerically enriched and, in the most favorable case, practically enantiomerically pure malonic acid monoesters.

α,α-Disubstituted malonic acid diesters can be selectively converted to enantiomerically enriched malonic acid monoesters with the aid of porcine liver esterase (M. Schneider et al., Angew. 96 [1984], 54). This gives good enantiomeric excesses when there is a marked difference in size between the substituents. α-Chymotrypsin is another useful enzyme for the enantioselective partial saponification of α,α-dialkylnialonic acid diesters to the corresponding α,α-dialkylmalonic acid monoesters (F. Björkling et al., Tetrahedron, 41 [1985], 1347).

This known enzyme-catalyzed partial hydrolysis could not be applied to α-monoalkylmalonic acid diesters. T. Kitazume et al. (J. Org. Chem., 51 [1986], 1003) were not able to obtain significant enantiomeric excesses because the monoesters in question immediately racemized under the reaction or working-up conditions.

A. L. Gutman et al. (J. Org. Chem., 57 [1992], 1063) obtained benzyl methyl α-methoxymalonate from dimethyl α-methoxymalonate with an enantiomeric excess of 98% by transesterification with benzyl alcohol using the lipase from Candida cylindracea as the transesterification catalyst. Monomethyl α-methoxymalonate could then be obtained by catalytic hydrogenation. This procedure is restricted to the methoxy compound and, as a two-stage process, is relatively expensive. Moreover, the configuration of the monoester is only stable in organic solvents.

SUMMARY OF THE INVENTION

The invention now provides enantiomerically enriched malonic acid monoesters α-monosubstituted by a tertiary hydrocarbon radical, or their salts, of the general formula I:

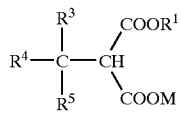

in which $R^1$, $R^3$, $R^4$ and $R^5$ are identical or different hydrocarbon radicals, and wherein any two of the radicals $R^3$, $R^4$ and $R^5$ may alternatively be present as a carbocyclic ring together with the quaternary carbon atom which they substitute, and M is hydrogen, one equivalent of a metal or an optionally substituted ammonium ion.

The invention further provides a process for the preparation of the enantiomerically enriched malonic acid monoesters α-monosubstituted by a tertiary hydrocarbon radical, or their salts, of the above general formula I, which comprises an enzymatic partial hydrolysis of α-monosubstituted malonic acid diesters of the general formula II:

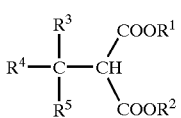

in which $R^1$, $R^3$, $R^4$ and $R^5$ are defined as indicated for the formula I and $R^2$ is also a hydrocarbon radical, which can differ from $R^1$.

DETAILED DESCRIPTION OF THE INVENTION

The process according to the invention produces the α-monosubstituted malonic acid monoesters I and their salts with good yields and a high enantioselectivity starting from the corresponding α-monosubstituted malonic acid diesters II, which are inexpensive and also readily available in industrial quantities. The tertiary hydrocarbon radical of the α-monosubstituted malonic acid diester II, with its quaternary carbon atom bonded to the a carbon atom of the malonic acid diester II, obviously allows enantioselective hydrolysis of only one of the carboxylic acid ester groups. The configuration of the enantiomerically enriched α-monosubstituted malonic acid monoesters is stable over a wide pH range. This is surprising because, according to the literature (T. Kitazume et al., loc. cit.), monosubstituted malonic acid diesters give racemic products on enzymatic saponification.

In the preferred α-monosubstituted malonic acid monoesters I, and accordingly also in the α-monosubstituted malonic acid diesters II preferred as starting materials, $R^1$ is a lower alkyl radical having 1 to 4 carbon atoms, especially 1 or 2 carbon atoms, or the benzyl radical and $R^3$, $R^4$ and $R^5$ are identical or different and are alkyl, alkenyl, aryl, alkaryl or aralkyl radicals having up to 10 carbon atoms. If any two of the radicals $R^3$, $R^4$ and $R^5$ form a carbocyclic ring with the quaternary carbon atom which they substitute, this ring preferably has a saturated hydrocarbon structure with 5 to 12 ring members, especially 5 or 6 ring members. M in the formula I is preferably hydrogen, one equivalent of an alkali metal or alkaline earth metal or an optionally alkyl-substituted ammonium ion. $R^2$ in the formula II has the same preferred meaning as $R^1$ and can differ from $R^1$.

If all three substituents $R^3$, $R^4$ and $R^5$ are different, the malonic acid esters have a center of chirality, so the α-monosubstituted malonic acid diesters II can be obtained as racemates or pure enantiomers. Both are suitable as starting materials for the process according to the invention. In the case of racemates, the enzymatic partial hydrolysis proceeds as a kinetic resolution of the racemates, thereby influencing the magnitude of the enantiomeric excess which can be achieved by the process of the invention. The enantiomeric excess is generally from 80 to >99%, depending on the substituents $R^3$, $R^4$ and $R^5$. The α-monosubstituted malonic acid diesters can be prepared from the unsubstituted malonic acid diesters in known manner by reaction with the appropriate electrophiles.

Examples of suitable malonic acid diesters II which may be mentioned are diethyl α-tert-butylmalonate, dimethyl α-tert-butylmalonate, dibenzyl α-tert-pentylmalonate, dimethyl α-tert-pentylmalonate, dimethyl α-(1-methyl-1-phenylethyl)malonate, diethyl α-(1-methyl-1-phenyl-n-propyl)malonate, dibutyl α-(1-ethyl-1-phenylethyl)malonate, diethyl α-(1-methylcyclohexyl)malonate and diethyl α-(1,1-dimethylprop-2-enyl)malonate.

Any known enzymes which hydrolyze carboxylic acid ester groups in aqueous media can be used as catalysts for the enzymatic partial hydrolysis. Any commercially available ester-cleaving enzymes, including esterases, lipases and proteases, are suitable for this purpose. They can be used in crystalline form, in aqueous suspension or fixed to a support. Examples of suitable enzymes include porcine liver esterase, the lipase from Candida cylindracea and α-chymotrypsin, already referred to above, the papain from Carica papaya and the lipase from porcine pancreas.

The process according to the invention is conveniently carried out by suspending the α-monosubstituted malonic acid diester II in water, an aqueous solution or a buffer solution affording optimal pH adjustment. Examples of suitable buffers are phosphate buffer, citrate buffer and tris(hydroxymethyl)aminomethane (abbreviated to "Tris"). They are generally used in concentrations of 0.01 to 3 M and conveniently in a weight ratio of 2 to 50, relative to the α-monosubstituted malonic acid diester II. The addition of a solvent, for example in amounts of up to about 40 percent by weight, based on the aqueous buffer solution, is helpful in many cases. Examples of suitable solvents are ethanol, tetrahydrofuran, dimethyl sulfoxide, N-methylpyrrolidone and acetonitrile.

The partial hydrolysis according to the invention takes place under the mild conditions typical of enzymatic reactions. The pH is advantageously kept in the range from about 4 to about 9 by the addition of a solution or suspension of a basic substance which provides hydroxyl ions. The optimal pH depends essentially on the enzyme used and can easily be determined by means of preliminary experiments. Examples of suitable basic substances are metal hydroxides or optionally substituted ammonium hydroxide. Dilute solutions, i.e., 0.05 to 2 N solutions, of alkali metal or alkaline earth metal hydroxides, alkali metal carbonates and/or alkali metal hydrogen carbonates are preferred. Appropriately diluted aqueous solutions of ammonia and of primary, secondary or tertiary alkylamines, such as methylamine, diethylamine or tributylamine, are also preferred as solutions which provide hydroxyl ions. The hydroxyl ions are required in molar quantities so that the α-monosubstituted malonic acid monoesters I are obtained in solution in the form of their corresponding salts at the end of the reaction.

The partial hydrolysis according to the invention generally takes place at atmospheric pressure, although it is also possible to apply elevated or reduced pressures, e.g. 0.7 to 2 bar. The hydrolysis remains partial under the conditions indicated, i.e., the second carboxylic acid ester group is not attacked.

The process can be carried out batchwise or continuously. In the batch procedure, it is possible, e.g., to place the α-monosubstituted malonic acid diester, the buffer solution, the enzyme and optionally a solvent in a stirred vessel, bring the mixture to the desired temperature and ensure thorough mixing by stirring. The amounts used in this procedure range from nanomoles to about 0.5 mol of α-monosubstituted malonic acid diester II per mg of enzyme. The pH of the mixture is monitored and kept in the indicated range by the addition of a solution which provides hydroxyl groups. The reaction mixture can be worked up by acidifying, e.g., with sulfuric or hydrochloric acid, filtering off the solid constituents, including the enzyme, and recovering the α-monosubstituted malonic acid monoester in solid form by extraction of the acid solution with a water-insoluble solvent, such as diethyl ether, and evaporation of the solvent from the ether solution, which has conveniently been dried beforehand. An alternative possibility is to separate off the enzyme by centrifugation or by means of a membrane process and then acidify the solution.

The enantiomeric excess can be determined in known manner, e.g., by converting the α-monosubstituted malonic acid monoester to the acid chloride, for example by means of cyanuric chloride, reacting said acid chloride with an optically active amine, for example, with S-phenylethylamine, to give the carboxamide, determining the ratio of the isomers by quantitative gas chromatographic analysis and using this to calculate the enantiomeric excess. The enantiomerically pure α-monosubstituted malonic acid monoesters can be obtained from the enantiomerically enriched products by means of conventional enantioselective or diastereoselective crystallization processes (E. L. Eliel, S. H. Wilen and L. N. Manden, Stereochemistry of Organic Compounds, John Wiley, 1994).

When the product separated from the reaction mixture as described, or an enantiomerically pure product, is dissolved in an aqueous solution of a basic substance, as illustrated previously, the corresponding salt of the α-monosubstituted malonic acid monoester I is obtained; said salt can be isolated as the solid product by evaporation of the solution, conveniently under vacuum, or reacted further in the solution.

The process according to the invention can be carried out continuously, e.g., by working in an enzyme membrane reactor by known methods or allowing a mixture of the buffer solution, the α-monosubstituted malonic acid diester II and optionally a solvent to trickle over an immobilized enzyme fixed in a reaction tube, with continuous monitoring of the pH, and working up the product stream as described previously, whereby separation of the enzyme naturally becomes superfluous.

The following Examples are intended to illustrate the invention further without limiting its scope as defined in the claims.

EXAMPLES

Example 1

3.0 g (13.9 mmol) of diethyl α-tert-butylmalonate are suspended in a mixture of 10 ml of 0.1 M aqueous potassium dihydrogen phosphate solution and 15 ml of 0.1 M aqueous disodium hydrogen phosphate solution. 1.3 ml of Chirazyme E1 (Boehringer Mannheim GmbH) are added to the suspension. The pH is monitored and 1 N sodium hydroxide solution is metered slowly into the stirred suspension, kept at room temperature, so that the 10 pH is in the range 6 to 9. 13 ml (13 mmol) of 1 N sodium hydroxide solution are consumed over 48 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 2.35 g (12.5 mmol) of monoethyl α-tertbutylmalonate, corresponding to a yield of 90% of theory. The enantiomeric excess is 96%.

Example 2

533 mg (2.83 mmol) of dimethyl α-tert-butylmalonate are suspended in a mixture of 5 ml of 0.1 M aqueous potassium dihydrogen phosphate solution and 7.5 ml of 0.1 M aqueous disodium hydrogen phosphate solution. 0.3 ml of porcine liver esterase (Boehringer Mannheim GmbH, catalog no. 104698) is added to the suspension. The pH is monitored and 1 N sodium hydroxide solution is metered slowly into the stirred suspension, kept at room temperature, so that the pH is in the range 6 to 9. 2.9 ml (2.9 mmol) of 1 N sodium hydroxide solution are consumed over 24 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 432 mg (2.48 mmol) of monomethyl α-tertbutylmalonate, corresponding to a yield of 85% of theory. The enantiomeric excess is 89%.

Example 3

500 mg (2.17 mmol) of diethyl α-tert-pentylmalonate are suspended in a mixture of 5 ml of 0.1 M aqueous potassium dihydrogen phosphate solution and 7.5 ml of 0.1 M aqueous disodium hydrogen phosphate solution. 0.3 ml of porcine liver esterase (Boehringer Mannheim GmbH, catalog no. 104698) is added to the suspension. The pH is monitored and 1 N sodium hydroxide solution is metered slowly into the stirred suspension, kept at room temperature, so that the pH is in the range 6 to 9. 2.2 ml (2.2 mmol) of 1 N sodium hydroxide solution are consumed over 24 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 334 mg (1.65 mmol) of monoethyl α-tertpentylmalonate, corresponding to a yield of 75% of theory. The enantiomeric excess is 82%.

Example 4

454 mg (1.67 inmol) of diethyl α-(1-methyl-1-phenylethyl)malonate are suspended in a mixture of 5 ml of 0.1 M aqueous potassium dihydrogen phosphate solution and 7.5 ml of 0.1 M aqueous disodium hydrogen phosphate solution. 0.4 ml of porcine liver esterase (Boehringer Mannheim GmbH, catalog no. 104698) is added to the suspension. The pH is monitored and 1 N sodium hydroxide solution is metered slowly into the stirred suspension, kept at room temperature, so that the pH is in the range 6 to 9. 1.7 ml (1.7 mmol) of 1 N sodium hydroxide solution are consumed over 24 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 340 mg (1.35 mmol) of monoethyl α-(1-methyl-1-phenylethyl)malonate, corresponding to a yield of 81% of theory. The enantiomeric excess is 94%.

Example 5

533 mg (2.83 mmol) of dimethyl α-tert-butylmalonate are suspended in a mixture of 10 ml of 0.1 M aqueous potassium dihydrogen phosphate solution and 15 ml of 0.1 M aqueous disodium hydrogen phosphate solution. 0.4 ml of porcine liver esterase (Boehringer Mannheim GmbH, catalog no. 104698) is added to the suspension. The pH is monitored and 1 N sodium hydroxide solution is metered slowly into the stirred suspension, kept at room temperature, so that the pH is in the range 6 to 9. 2.8 ml (2.8 mmol) of 1 N sodium hydroxide solution are consumed over 30 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 432 mg (2.48 mmol) of monomethyl α-tert-butylmalonate, corresponding to a yield of 87% of theory. The enantiomeric excess is 89%.

Example 6

476 mg (1.9 mmol) of dimethyl α-(1-methyl-1-phenylethyl)malonate are suspended in a mixture of 10 ml of 0.1 M aqueous potassium dihydrogen phosphate solution and 15 ml of 0.1 M aqueous disodium hydrogen phosphate solution. 0.5 ml of porcine liver esterase (Boehringer Mannheim GmbH, catalog no. 104698) is added to the suspension. The pH is monitored and 1 N sodium hydroxide solution is metered slowly into the stirred suspension, kept at room temperature, so that the pH is in the range 6 to 9. 1.6 ml (1.6 mmol) of 1 N sodium hydroxide solution are consumed over 30 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 305 mg (1.29 mmol) of monomethyl α-(1-methyl-1-(1-methyl-1-phenylethyl)malonate, corresponding to a yield of 68% of theory. The enantiomeric excess is 90%.

Example 7

500 mg (1.9 mmol) of dimethyl α-(1-methylcyclohexyl)malonate are suspended in a mixture of 10 ml of 0.1 M aqueous potassium dihydrogen phosphate solution and 15 ml of 0.1 M aqueous disodium hydrogen phosphate solution. 0.5 ml of porcine liver esterase (Boehringer Mannheim GmbH, catalog no. 104698) is added to the suspension. The pH is monitored and 1 N sodium hydroxide solution is metered slowly into the stirred suspension, kept at room temperature, so that the pH is in the range 6 to 9. 1.9 ml (1.9 mmol) of 1 N sodium hydroxide solution are consumed over 40 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 400 mg (1.76 mmol) of monomethyl α-(1-methylcyclohexyl)malonate, corresponding to a yield of 90% of theory. The enantiomeric excess is 96%.

The disclosure of Germany priority patent application 196 23 142.6, filed Jun. 10, 1996, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by letters patent of the united states is:

1. A mixture of enantiomers of a malonic acid monoester α-monosubstituted by a tertiary hydrocarbon radical, of its salts, or the general formula I:

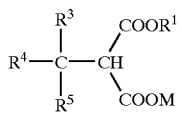

I in which $R^1$, $R^3$, $R^4$ and $R^5$ are identical or different hydrocarbon radicals, and wherein any two of the radicals $R^3$, $R^4$ and $R^5$ may alternatively be present as a carbocyclic ring together with the quaternary carbon atom which they substitute, and M is hydrogen, one equivalent of a metal or an optionally substituted ammonium ion, wherein one enantiomer is present in an amount in excess of an amount of the other enantiomer.

2. The mixture as claimed in claim 1 wherein $R^1$ is an alkyl radical having 1 to 4 carbon atoms or a benzyl radical, $R^3$, $R^4$ and $R^5$ are identical or different alkyl, alkenyl, aryl, alkaryl or aralkyl radicals having up to 10 carbon atoms, and wherein any two of the radicals $R^3$, $R^4$ and $R^5$ may alternatively be present as a carbocyclic ring having 5 to 12 carbon atoms together with the quaternary carbon atom which they substitute, and M is hydrogen, one equivalent of an alkali metal or alkaline earth metal or an optionally alkyl substituted ammonium ion.

3. A process for the preparation of an enantiomerically enriched malonic acid monoester (α-monosubstituted by a tertiary hydrocarbon radical, or its salts, of the general formula I:

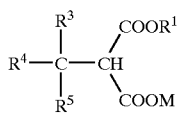

I in which $R^1$, $R^3$, $R^4$ and $R^5$ are identical or different hydrocarbon radicals, and wherein any two of the radicals $R^3$, $R^4$ and $R^5$ may alternatively be present as a carbocyclic ring together with the quaternary carbon atom which they substitute, and M is hydrogen, one equivalent of a metal or an optionally substituted ammonium ion, said process comprising an enzymatic partial hydrolysis of α-monosubstituted malonic acid diesters of the general formula II:

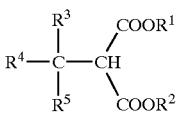

II in which $R^1$, $R^3$, $R^4$ and $R^5$ are defined as indicated for the formula I and Re is also a hydrocarbon radical, which can differ from R.

4. The process for the preparation of an enantiomerically enriched malonic acid monoester α-monosubstituted by a tertiary hydrocarbon radical, or its salts, of the general formula I as claimed in claim 3 wherein $R^1$ is an alkyl radical having 1 to 4 carbon atoms or a benzyl radical, $R^3$, $R^4$ and $R^5$ are identical or different alkyl, alkenyl, aryl, alkaryl or aralkyl radicals having up to 10 carbon atoms, and wherein any two of the radicals $R^3$, $R^4$ and $R^5$ may alternatively be present as a carbocyclic ring having 5 to 12 carbon atoms together with the quaternary carbon atom which they substitute, and M is hydrogen, one equivalent of an alkali metal or alkaline earth metal or an optionally alkyl-substituted ammonium ion.

5. The process as claimed in claim 3 wherein an enzyme selected from the group consisting of esterases, lipases, proteases and other ester-cleaving enzymes is used as a catalyst for the enzymatic partial hydrolysis.

6. The process as claimed in claim 4 wherein an enzyme selected from the group consisting of esterases, lipases, proteases and other ester-cleaving enzymes is used as a catalyst for the enzymatic partial hydrolysis.

7. The process as claimed in claim 3 wherein the enzymatic partial hydrolysis is carried out in water, an aqueous solution or a buffer solution, and a solution or suspension of a basic substance which provides hydroxyl ions is optionally added in an amount to optimize the pH for the particular enzyme.

8. The process as claimed in claim 4 wherein the enzymatic partial hydrolysis is carried out in water, an aqueous solution or a buffer solution, and a solution or suspension of a basic substance which provides hydroxyl ions is optionally added in an amount to optimize the pH for the particular enzyme.

9. The process as claimed in claim 5 wherein the enzymatic partial hydrolysis is carried out in water, an aqueous solution or a buffer solution, and a solution or suspension of a basic substance which provides hydroxyl ions is optionally added in an amount to optimize the pH for the particular enzyme.

10. The process as claimed in claim 6 wherein the enzymatic partial hydrolysis is carried out in water, an aqueous solution or a buffer solution, and a solution or suspension of a basic substance which provides hydroxyl ions is optionally added in an amount to optimize the pH for the particular enzyme.

11. The process as claimed in claim 7 wherein the basic substance is an alkali metal or alkaline earth metal hydroxide, an alkali metal carbonate or alkali metal hydrogen carbonate or optionally alkyl-substituted ammonium hydroxide.

12. The process as claimed in claim 8 wherein the basic substance is an alkali metal or alkaline earth metal hydroxide, an alkali metal carbonate or alkali metal hydrogen carbonate or optionally alkyl-substituted ammonium hydroxide.

13. The process as claimed in claim 9 wherein the basic substance is an alkali metal or alkaline earth metal hydroxide, an alkali metal carbonate or alkali metal hydrogen carbonate or optionally alkyl-substituted ammonium hydroxide.

14. The process as claimed in claim 10 wherein the basic substance is an alkali metal or alkaline earth metal hydroxide, an alkali metal carbonate or alkali metal hydrogen carbonate or optionally alkyl-substituted ammonium hydroxide.

15. The process as claimed in claim 3 wherein a water-soluble solvent is used during the enzymatic partial hydrolysis.

16. The process as claimed in claim 3 wherein the enzymatic partial hydrolysis is carried out at a temperature of 15 to 50° C., and under a pressure of 0.8 bar to 2.0 bar.

17. The process as claimed in claim 16 wherein the enzymatic partial hydrolysis is carried out at a temperature of 20 to 30° C.

18. The process as claimed in claim 7, comprising carrying out the enzymatic partial hydrolysis at a pH of 4–9 to form a reaction mixture, acidifying the mixture, and then extracting the α-monosubstituted malonic acid monoester I with a water-insoluble solvent, optionally after solids have been separated off.

19. The process as claimed in claim 11, comprising carrying out the enzymatic partial hydrolysis at a pH of 4–9 to form a reaction mixture, acidifying the mixture, and then extracting the α-monosubstituted malonic acid monoester I with a water-insoluble solvent, optionally after solids have been separated off.

20. The process as claimed in claim 15, comprising carrying out the enzymatic partial hydrolysis at a pH of 4–9 to form a reaction mixture, acidifying the mixture, and then extracting the α-monosubstituted malonic acid monoester I with a water-insoluble solvent, optionally after solids have been separated off.

21. The mixture of claim 1, wherein one of the enantiomers is present in an amount of at least 80% of the mixture.

22. The mixture of claim 1, wherein the malonic acid monoester is selected from the group consisting of monoethyl α-tert-butylmalonate, monomethyl α-tert-butylmalonate, monobenzyl α-tert-pentylmalonate, monomethyl α-tert-pentylmalonate, monomethyl α-(1methyl-1-phenylethyl)malonate, monoethyl α-(1-methyl-1-phenyl-n-propyl)malonate, monobutyl α-(1-ethyl-1-phenylethyl)malonate, monoethyl α-(1-methylcyclohexyl)malonate and monoethyl α-(1,1-dimethylprop-2-enyl)malonate.

23. A mixture of enantiomers of a malonic acid monoester α-monosubstituted by a tertiary hydrocarbon radical, or its salts, of the general formula I:

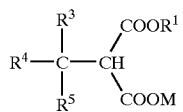

I in which $R^1$, $R^3$, $R^4$ and $R^5$ are identical or different hydrocarbon radicals, and wherein any two of the radicals $R^3$, $R^4$ and $R^5$ may alternatively be present as a carbocyclic ring together with the quaternary carbon atom which they substitute, and M is hydrogen, one equivalent of a metal or an optionally substituted ammonium ion, wherein one enantiomer is present in an amount in excess of an amount of the other enantiomer, obtained by a process comprising an enzymatic partial hydrolysis of α-monosubstituted malonic acid diesters of the general formula II:

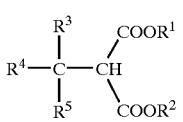

II in which $R^1$, $R^3$, $R^4$ and $R^5$ are defined as indicated for the formula I and $R^2$ is also a hydrocarbon radical, which can differ from $R^1$.

* * * * *